US00PP12067P2

(12) United States Plant Patent
Moore

(10) Patent No.: US PP12,067 P2
(45) Date of Patent: Aug. 28, 2001

(54) STRAWBERRY PLANT NAMED 'SCHWARTZE'

(75) Inventor: Patrick P. Moore, Puyallup, WA (US)

(73) Assignee: Washington State University Research Foundation, Pullman, WA (US)

( * ) Notice: Subject to any disclaimer, the term of this patent is extended or adjusted under 35 U.S.C. 154(b) by 0 days.

(21) Appl. No.: 09/211,999

(22) Filed: Dec. 14, 1998

(51) Int. Cl.[7] ..... A01H 5/00
(52) U.S. Cl. ..... Plt./208
(58) Field of Search ..... Plt./208

(56) References Cited

U.S. PATENT DOCUMENTS

P.P. 2,085 * 9/1961 Ulrich ..... Plt./208
P.P. 2,884 * 5/1969 Hagerstrom ..... Plt./208

* cited by examiner

*Primary Examiner*—Bruce R. Campell
*Assistant Examiner*—Wendy C Baker
(74) *Attorney, Agent, or Firm*—Townsend and Townsend and Crew, LLP

(57) ABSTRACT

'Schwartze' is characterized by fruit which is large, firm, easily capped and very late seasoned. The fruit is high in yield, has excellent flesh flavor, and very low levels of preharvest fruit rot.

6 Drawing Sheets

DESCRIPTION

This invention relates to a new and distinct short day, June bearing variety of strawberry plant named 'Schwartze'. The variety is botanically identified as *Fragaria ananassa* Duch.

The variety was reproduced asexually by stolons or runners in observation plots at WSU Puyallup, Wash. The genealogy of 'Schwartze' is shown in FIG. 4.

'Schwartze' was selected from a cross 'Nanaimo'×ORUS 1076-124 made in 1993. ORUS 1076-124 is a full sib of ORUS 1076-126 released in 1997 as 'Independence'. 'Schwartze', designated by the breeder as WSU 2310, was selected at WSU Puyallup in 1995.

'Schwartze' was propagated and planted in a replicated planting of 3 plots of 10 plants/clone at WSU Puyallup in 1996 and harvested for the first time in 1997 with other plantings. (Table 1) None of the cultivars listed herein is patented or is the subject of a pending application for patent, except 'Puget Reliance', U.S. Plant Pat. No. 9,310.

TABLE 1

1997 harvest of 1996 planted strawberries, Puyallup, WA

| Clone | Yield (t/a) | | Fruit Weight (g) | | Fruit[1] Rot (%) | |
|---|---|---|---|---|---|---|
| WSU2306 | 15.2 | A | 19.1 | A | 36% | A–F |
| Schwartze | 14.1 | A | 15.8 | B | 14% | G |
| WSU 2247 | 13.0 | A B | 14.8 | B C | 38% | A–E |
| WSU 2325 | 12.7 | A–C | 14.4 | B–E | 22% | F G |
| WSU 2263 | 12.5 | A–D | 11.4 | E–H | 39% | A–E |
| WSU 2315 | 10.3 | B–E | 11.8 | C–H | 22% | F G |
| WSU 2323 | 10.2 | B–E | 11.9 | C–H | 25% | E–G |
| NANAIMO** | 10.2 | | 14.2 | | 29% | |
| WSU 2299 | 9.9 | B–F | 13.3 | B–F | 28% | C–F |
| ORUS 1267-236** | 9.8 | | 13.1 | | 51% | |
| WSU 2288 | 9.5 | C–F | 16.2 | B | 30% | B–F |
| WSU 2300 | 9.5 | C–F | 15.3 | B | 27% | D–G |
| Redcrest | 9.4 | C–F | 12.2 | C–G | 35% | A–F |
| WSU 2319 | 9.3 | D–F | 11.6 | D–H | 30% | B–F |
| WSU 2249 | 9.1 | D–F | 13.3 | B–F | 40% | A–D |
| WSU 2317 | 9.0 | E F | 14.7 | B–D | 33% | A–F |

TABLE 1-continued 1997 harvest of 1996 planted strawberries, Puyallup, WA

| | | | | | | |
|---|---|---|---|---|---|---|
| WSU 2318 | 8.9 | D F | 9.1 | H | 30% | B–F |
| Totem | 8.5 | E–F | 12.1 | C–H | 43% | A B |
| Independence** | 8.3 | | 13.6 | | 26% | |
| WSU 2326 | 8.3 | E–G | 10.7 | F–H | 36% | A–E |
| Hood | 7.6 | E–G | 10.6 | F–H | 37% | A–E |
| Sumas | 7.5 | E–G | 11.6 | D–H | 45% | A |
| WSU 2324 | 6.5 | F G | 10.3 | F–H | 30% | B–F |
| WSU 2301 | 5.4 | G H | 10.4 | F–H | 37% | A–E |
| WSU 2309 | 5.4 | G H | 9.3 | G H | 42% | A–C |
| WSU 2321 | 3.2 | H | 10.0 | G H | 45% | A |
| Average | 9.4 | | 12.7 | | 33% | |

| Clone | Fruit[2] Firmness (g) | | Midpoint of Harvest | | Drip Loss (%)[z] | |
|---|---|---|---|---|---|---|
| WSU2306 | 175 | F–H | 6/16 | C B | 34.7% | A |
| Schwartze | 202 | B–G | 6/22 | A | 34.7% | A |
| WSU 2247 | 207 | A–F | 6/13 | E D | | |
| WSU 2325 | 185 | E–H | 6/8 | G F | 36.0% | A |
| WSU 2263 | 244 | A | 6/7 | G | 35.5% | A |
| WSU 2315 | 190 | D–H | 6/15 | C D | 34.3% | A |
| WSU 2323 | 209 | A–F | 6/14 | C D | | |
| NANAIMO** | 169 | | 6/12 | | 35.3% | |
| WSU 2299 | 188 | D–H | 6/13 | C D | 34.2% | A |
| ORUS 1267-236** | 168 | | 6/15 | | 33.8% | |
| WSU 2288 | 228 | A–C | 6/13 | | | |
| WSU 2300 | 235 | A B | 6/18 | B | | |
| Redcrest | 228 | A–C | 6/16 | C B | 33.5% | A |
| WSU 2319 | 167 | G H | 6/15 | C D | 36.2% | A |
| WSU 2249 | 203 | B–G | 6/7 | | | |
| WSU 2317 | 178 | F–H | 6/12 | | 36.0% | A |
| WSU 2318 | 225 | A–D | 6/16 | C B | | |
| Totem | 188 | D–H | 6/8 | G F | 34.0% | A |
| Independence** | 213 | | 6/18 | | 31.6% | |
| WSU 2326 | 163 | H | 6/14 | | 34.9% | A |
| Hood | 195 | C–H | 6/10 | E F | 36.8% | A |
| Sumas | 176 | F–H | 6/10 | G F | 36.4% | A |
| WSU 2324 | 220 | A–E | 6/13 | C D | | |
| WSU 2301 | 163 | H | 6/14 | C D | | |

TABLE 1-continued

| 1997 harvest of 1996 planted strawberries, Puyallup, WA | | | | | |
|---|---|---|---|---|---|
| WSU 2309 | 172 | F–H | 6/8 | G F | |
| WSU 2321 | 175 | F–H | 6/12 | | |
| Average | 195 | | 6/13 | | 34.9% |

Values are means of three 10 foot plots, except clones indicated by ** which are means of two plots. Means within a column followed by the same letter are not significantly different using Duncan's Multiple Range Test, P = 0.05.
[1]"Fruit rot" is the percent of rot at time of harvest by weight, mostly due to *botrytis cinera*.
[2]Fruit firmness was measured as the force required for a 4-mm-diameter cylinder to penetrate the shoulder of a fruit to the depth of 6 mm. Firmness was measured using a Hunter Spring mechanical force gauge (series L; Ametek, Hatfield, Pa.) for five fruit per plot at each harvest. The weighted mean was calculated for the harvest season specified.
[z]Drip loss measurements on sliced, sugared (4 + 1), frozen fruit.

In 1997, the plots of 'Schwartze' were vigorous and productive. The fruit was large, firm, easily capped and very late season. The fruit weight and the yield of 'Schwartze' were both significantly greater than that of any named cultivar in the planting. 'Schwartze' also had the lowest percentage of fruit rot. The midpoint of harvest was 4 days later than that of 'Independence' recently released partially because it produced fruit later in the season than other Pacific Northwest cultivars. A graph of the yield through the season for 'Schwartze', 'Totem', 'Redcrest' and 'Independence' is given in FIG. 5. The plots were harvested for a second season in 1998. Several of the clones (including 'Schwartze') were used as parents in pollinations and as a result only two plots/clone were harvested for 10 clones. These clones were analyzed statistically separately from the clones represented by 3 plots. Yield of 'Schwartze' in 1998 was similar to 1997 (Table 2).

TABLE 2

| 1997–98 Harvest data for 1996 planted strawberries, Puyllaup, WA | Yield (t/a) | | | | | |
|---|---|---|---|---|---|---|
| | 1998 | | 1997 | | Total | |
| Clones with 3 replications | | | | | | |
| ORUS 1267-236 | 17.7 | A | 9.8 | A | 27.5 | A |
| WSU 2247 | 12.0 | B C | 13.0 | A | 25.0 | A B |
| Totem | 14.5 | A B | 8.5 | A | 23.0 | A–C |
| Independence | 12.8 | B | 8.3 | A | 21.2 | A–C |
| WSU 2319 | 10.4 | B–D | 9.3 | A | 19.7 | B–D |
| WSU 2249 | 10.5 | B–D | 9.1 | A | 19.5 | B–D |
| WSU 2299 | 8.8 | C D | 9.9 | A | 18.4 | B–D |
| WSU 2323 | 7.0 | D | 10.2 | A | 17.2 | C D |
| WSU 2317 | 7.8 | D | 9.0 | A | 16.7 | C D |
| Hood | 6.4 | D | 7.6 | A | 14.1 | D |
| Clones with 2 replications | | | | | | |
| WSU 2306 | 16.6 | A | 14.8 | A | 32.4 | A |
| WSU 2325 | 15.4 | A B | 13.8 | A | 29.2 | A B |
| | 16.1 | A | 12.7 | A | 28.7 | A–C |
| Schwartze | 13.9 | A–C | 13.8 | A | 27.7 | A–D |
| WSU 2300 | 13.2 | A–C | 10.5 | A | 23.7 | B–E |
| WSU 2288 | 10.6 | A–C | 10.6 | A | 21.2 | B–E |
| WSU 2315 | 11.2 | A–C | 9.9 | A | 21.0 | C–E |
| Redcrest | 9.4 | A–C | 10.8 | A | 20.0 | D E |
| Nanalmo | 8.9 | B C | 10.2 | A | 19.1 | E |
| Sumas | 11.8 | A–C | 8.9 | A | 18.7 | E |
| Average | 11.7 | | 10.5 | | 22.2 | |

TABLE 2-continued

| 1997–98 Harvest data for 1996 planted strawberries, Puyllaup, WA | Weight (g) | | Fruit Fruit Rot (%) | | Fruit Firmness (g) | |
|---|---|---|---|---|---|---|
| Clones with 3 replications | | | | | | |
| ORUS 1267-236 | 11.8 | A B | 37.3 | A | 163 | B–D |
| WSU 2247 | 11.0 | A–C | 33.5 | A B | 195 | A B |
| Totem | 10.8 | A–C | 21.2 | C D | 191 | A–C |
| Independence | 8.7 | C | 20.8 | C D | 217 | A |
| WSU 2319 | 10.7 | A–C | 27.4 | A–C | 153 | D |
| WSU 2249 | 10.9 | A–C | 25.6 | B C | 174 | B–D |
| WSU 2299 | 9.0 | B C | 13.6 | D | 184 | A–D |
| WSU 2323 | 9.5 | A–C | 20.1 | C D | 196 | A B |
| WSU 2317 | 12.4 | A | 27.5 | A–C | 177 | B–D |
| Hood | 9.9 | A–C | 24.3 | B–D | 155 | C D |
| Clones with 2 replications | | | | | | |
| WSU 2306 | 14.3 | A | 21.1 | A–C | 197 | B–D |
| WSU 2325 | 11.7 | B C | 13.6 | C D | 165 | D |
| | 11.3 | B C | 24.6 | A B | 240 | A B |
| Schwartze | 7.3 | E | 7.5 | D | 158 | D |
| WSU 2300 | 11.6 | B C | 26.4 | A | 201 | B–D |
| WSU 2288 | 13.1 | A B | 16.7 | B C | 227 | A–C |
| WSU 2315 | 9.0 | D E | 13.4 | C D | 192 | C D |
| Redcrest | 9.1 | D E | 19.2 | A–C | 264 | A |
| Nanalmo | 10.0 | C D | 19.8 | A–C | 167 | D |
| Sumas | 10.2 | C D | 24.5 | A B | 157 | D |
| Average | 10.6 | | 21.9 | | 189 | |

| | Harvest Season | | | | | | | |
|---|---|---|---|---|---|---|---|---|
| | 5% Harvest | | 50% Harvest | | 95% Harvest | | Length of Season | |
| 1 Clones with 3 replications | | | | | | | | |
| ORUS 1267-236 | 6/10 | B | 6/21 | B | 7/7 | A | 27 | A B |
| WSU 2247 | 6/6 | D–F | 6/15 | E F | 7/1 | B | 25 | A B |
| Totem | 6/7 | C–E | 6/16 | D E | 7/1 | B | 24 | A B |
| Independence | 6/21 | A | 6/27 | A | 7/7 | A | 17 | C |
| WSU 2319 | 6/4 | F | 6/13 | E F | 6/30 | B C | 26 | A B |
| WSU 2249 | 6/5 | E F | 6/12 | E F | 6/26 | C D | 21 | B C |
| WSU 2299 | 6/9 | B–D | 6/18 | C D | 7/1 | B | 22 | A B |
| WSU 2323 | 6/9 | B C | 6/23 | B | 7/7 | A | 28 | A |
| WSU 2317 | 6/3 | F | 6/11 | F | 6/25 | D | 22 | A B |
| Hood | 6/4 | F | 6/13 | E F | 6/30 | B | 26 | A B |
| Clones with 2 replications | | | | | | | | |
| WSU 2306 | 6/14 | B | 6/25 | C | 7/12 | A B | 29 | A |
| WSU 2325 | 6/2 | D | 6/12 | F | 6/26 | D | 26 | A |
| | 6/3 | D | 6/13 | F | 7/1 | C D | 28 | A |
| Schwartze | 6/21 | A | 7/2 | A | 7/14 | A | 23 | A B |
| WSU 2300 | 6/19 | A | 6/28 | B | 7/7 | A–C | 19 | B |
| WSU 2288 | 6/10 | C | 6/22 | D | 7/4 | C D | 25 | A B |
| WSU 2315 | 6/13 | B | 6/21 | D | 7/1 | C D | 18 | B |
| Redcrest | 6/8 | C | 6/18 | E | 7/4 | C D | 27 | A |
| Nanalmo | 6/8 | C | 6/16 | E | 7/6 | B–D | 28 | A |
| Sumas | 6/3 | D | 6/12 | F | 7/1 | C D | 28 | A |
| Average | 6/9 | | 6/18 | | 7/3 | | 24 | |

Values represent means of two or three replications of 10 foot plots. Those represented by two replications were used in pollination in 1998 Means within a column followed by the same letter are not significantly different using Duncan's Multiple Range Test, P = 0.05

Some clones in the planting had greater yield than 'Schwartze', but were not statistically greater. Fruit weight of 'Schwartze' was much smaller in the second harvest season than in the first. 'Schwartze' had the smallest amount of fruit rot again in 1998. The midpoint of the harvest season for 'Schwartze' was five days later than the 'Independence'.

The fruit yield for each harvest in 1998 for 'Schwartze' compared to other cultivars is given in FIG. 6. The fruit of 'Schwartze' has an excellent red exterior color and good internal color. At field days, growers found the fresh flavor excellent. Fruit flavor is best described as sweet with a full strawberry flavor.

The plant of 'Schwartze' is very vigorous and runners readily. It forms a uniform, vigorous, dense matted row. In the first season 'Schwartze' had large fruit, but was small in the second fruiting season. Cultural practices may need to be modified to promote larger fruit size in the second season. For example, the row may need to be narrowed or irrigation increased or some other treatment may be necessary to promote larger fruit size. The plots appeared very uniform and vigorous after the second harvest season, indicating 'Schwartze' likely has a high level of virus tolerance.

'Schwartze' differs from its parents in a number of ways. For example, 'Nanaimo' is a mid-season cultivar whereas 'Schwartze' ripens much later. The mid-point harvest for 'Nanaimo' was Jun. 12, 1997 and the mid-point harvest for 'Schwartze' was June 22. In 1998, the mid-point harvest for 'Nanaimo' was June 16 while for 'Schwartze' it was July 2. The shape of the fruit of 'Schwartze' also differs from 'Nanaimo' in that 'Nanaimo's' fruit is longer and often more pointed than that of 'Schwartze'. 'Schwartze' also distinguishes from 'Nanaimo' in that its petioles and petiolules are longer.

Referring to 'Schwartze's' other parent, 'ORUS 1076-124', while there is a similarity in harvest season, the fruit of 'ORUS 1076-124' is rough and difficult to cap (calyx removal), while 'Schwartze' is usually symmetrical and caps easily. 'ORUS 1076-124' has a higher than average level of fruit rot while 'Schwartze', in both the years 1997 and 1998 at WSU Puyallup, had the lowest amount of fruit rot. A marked distinction between 'Schwartze' and 'ORUS 1076-124' is that the flowers of 'ORUS 1076-124' are above the leaf canopy, while the flowers of 'Schwartze' are borne below the canopy.

The colors illustrated are as close as it reasonably possible to obtain in a photographic illustration of this character with respect to the light reflectance visible in FIG. 3.

IN THE DRAWINGS

FIG. 1 shows leaves typical of the new variety having slight cupping.

FIG. 2 illustrates leaves of the new variety slightly pressed to allow for good photography.

FIG. 3 depicts typical fruit of the new variety showing fruit shape and fruit held above the ground.

Figure 4:
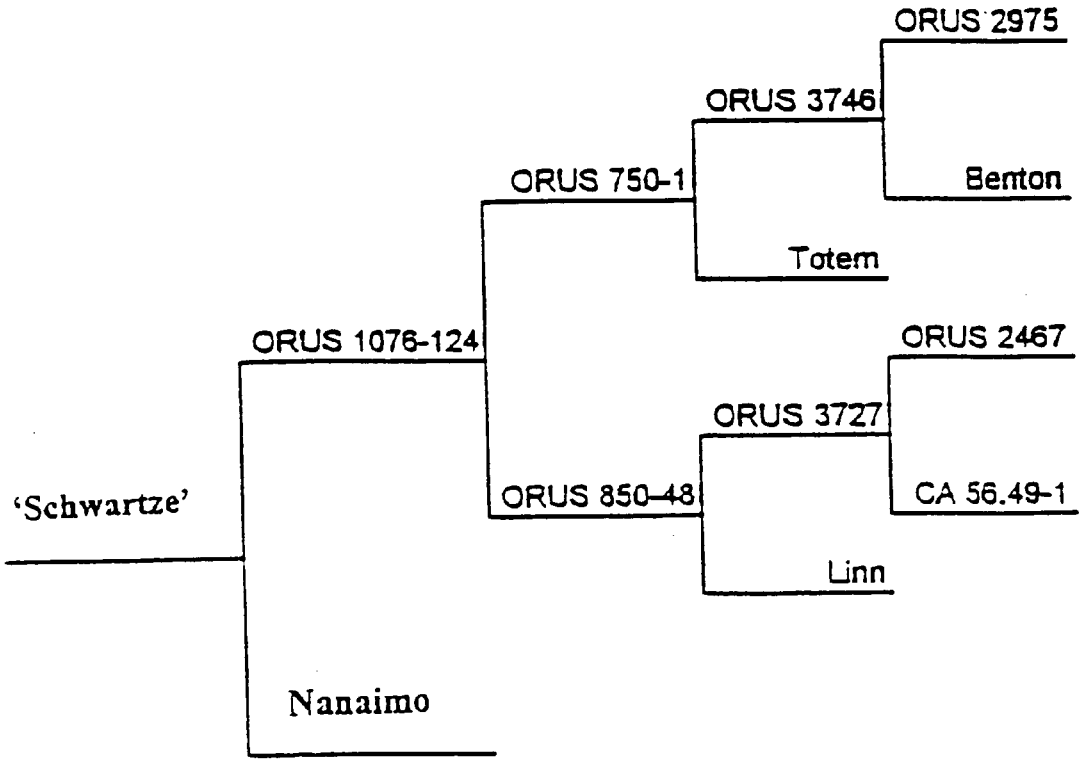

FIG. 4 sets forth the genealogy of 'Schwartze'.

FIG. 5 is a graph of the yield through the season for 'Schwartze', 'Totem', 'Redcrest', and 'Independence'.

FIG. 6 is a graph of the fruit yielded for each harvest in 1998 for 'Schwartze' compared with other cultivars.

The performance in 1998 at WSU Puyallup was very promising. In summary, 'Schwartze' has four strong points, namely:

1. High yields.
2. Extremely late fruit production, with midpoint of harvest 5 days after 'Independence'.
3. Excellent fresh flavor.
4. Very low levels of preharvest fruit rot.

The primary interest in 'Schwartze' is as a late season fresh market cultivar that would extend the Pacific Northwest strawberry season. The fruit qualities should also allow it to be used for processing. However, the time of fruit production may limit use for processing.

'Schwartze' can be clearly distinguished from other Pacific Northwest cultivars by its late fruiting season. It can be distinguished vegetatively from other Pacific Northwest cultivars except 'Independence' by the width of the central leaflet and the ratio of the length/width of the central leaflet. It can be distinguished from 'Independence' by the position of its flowers relative to the position of leaves. 'Schwartze' can be distinguished from all of the Pacific Northwest cultivars by the length of the petiole or length of the petiolule.

SPECIFIC DESCRIPTION

With the exception of the flower petal colors, the color terminology below is in accordance with the Munsell color system. The color terminology for the flower petal colors is according to the chart of The Royal Horticultural Society.

Plant: Large and vigorous. Produces abundant runners. Forms a very dense matted row. The plant, as measured in 1998 and 1999 plantings at Puyallup had a canopy cross section of 2.88 sq. ft. with a width of 35 in. at a height of 14 in. The plant forms a very dense canopy.

Leaves: Leaves of 'Schwartze' are shown in FIGS. 1 and 2. They are medium in size and slightly cupped. Leaf characteristics of 'Schwartze' are compared to other Pacific Northwest varieties in Table. 3.

TABLE 3

Leaf characteristics of selected Pacific Northwest strawberry cultivars planted June, 1998, Puyallup, WA
Data collected Aug. 28–Sept. 1, 1998

| | Measurements on central leaflet | | | |
|---|---|---|---|---|
| Clone | Length (cm) | Width (cm) | Ratio L/W | Number Serrations |
| Firecracker | 8.9 A B | 7.6 A–C | 1.18 B–D | 20.0 C–E |
| Hood | 7.3 E F | 6.6 D E | 1.12 D E | 18.9 D E |
| Independence | 7.7 C–E | 6.3 E | 1.22 B | 21.9 B C |
| Puget Reliance | 6.8 F | 5.2 F | 1.32 A | 17.8 E |
| Rainier | 9.4 A | 8.1 A | 1.16 B–D | 22.7 B |
| Redcrest | 8.3 B–D | 7.3 B–D | 1.14 C–E | 23.1 B |
| Sumas | 8.6 A–C | 8.0 A B | 1.07 E | 26.3 A |
| Totem | 7.9 C–E | 7.2 C D | 1.10 D E | 22.8 B |
| Schwartze | 7.5 D–F | 6.2 E | 1.21 B C | 21.1 B–D |

| | Measurements on central leaflet Leaf Color | | Petiolule | Petiolule |
|---|---|---|---|---|
| Clone | Upper Surface | Lower Surface | Length (mm) | Length (cm) |
| Firecracker | 7.5GY 3/2 | 5GY 5/3 | 11.3 B | 17.1 B C |
| Hood | 7.5GY 4/3 | 5GY 5/3 | 6.0 D | 15.0 B C |
| Independence | 7.5GY 4/2 | 5GY 5/3 | 7.3 C | 13.3 C D |
| Puget Reliance | 7.5GY 4/3 | 5GY 5/3 | 8.7 C | 14.0 C |
| Rainier | 7.5GY 3/2 | 2.5GY 5/3 | 7.0 C | 13.6 C D |
| Redcrest | 7.5GY 4/2 | 5GY 5/3 | 8.0 C | 15.9 B C D |
| Sumas | 7.5GY 3/3 | 5GY 5/3 | 6.4 D | 17.9 B |

TABLE 3-continued

Leaf characteristics of selected Pacific Northwest strawberry cultivars planted June, 1998, Puyallup, WA
Data collected Aug. 28–Sept. 1, 1998

| | | | | |
|---|---|---|---|---|
| Totem | 7.5GY 4/3 | 5GY 5/3 | 9.1 C | 16.9 B C |
| Schwartze | 7.5GY 3/2 | 5GY 5/3 | 13.8 A | 21.7 A |

Means based on 5 leaves/clone for leaf color and petiole length and 10 leaves/clone for all other characteristics.
Means followed by the same letter within a column are not significantly different using Duncans Multiple Range Test, P = 0.05.

The length of the central leaflet of 'Schwartze' is shorter than 'Firecracker', 'Rainier' and 'Sumas', but does not differ significantly from the other Pacific Northwest varieties. The width of the central leaflet was narrower than 'Firecracker', 'Rainier', 'Redcrest', 'Sumas', and 'Totem' and wider than 'Puget Reliance'. It did not differ significantly from 'Hood' or 'Independence'. The ratio of length/width of the central leaflet for 'Schwartze' was greater than that for 'Hood', 'Sumas' and 'Totem' and less than that for 'Puget Reliance'. The angle between the leaf blade of the central leaflet and the petiole was greater tha 90°. The number of serrations of the central leaflet for 'Schwartze' were less than that for 'Sumas' and more than that for 'Puget Reliance'. The serration's on the leaf begin about ¼ of the way from the petiolule. The hairs of the petiole usually point toward the base of the petiole, but often are at 90° to the axis of the petiole. The leaves rarely have leaflet bracts on the petiole. The most distinguishing characteristics of 'Schwartze' is the length of the petiole and the length of the petiolule. 'Schwartze' has longer petioles and petiolules than any other Pacific Northwest variety. There was little variation in the color of the upper and lower surfaces of the leaves among Pacific Northwest varieties. The color of the upper leaf surface of 'Schwartze' was 7.5GY 3/2 and the lower surface was 5GY 5/3. The leaves of 'Schwartze' have three leaflets. The angle between the terminal leaflet base and the petiolule is approximately 135°. The shape of the terminal leaflet is oval to orbicular with a rounded apex and is coarsely serrated. There was sparse pubescense along the leaflet margin and along the veins on the lower surface of the leave. The upper surface of the leaves was glabrous. The number of serrations is given on Table 3 as 21.1. The leaflet base shape is acute. The angle of the base of the terminal leaflet and the petiolule is approximately 135°.

Fruit: 'Schwartze' is a short day plant, producing fruit in June and July at Puyallup, Wash. The fruit is usually smooth and symmetrically conic with inserted achenes (FIG. 3). Fruit is usually held up off the ground. The external color of 'Schwartze' measured on Jul. 31, 1998 was 5R 3/8. Fruit color varied with in a fruit from 2.5R 3/7 to 5R 4/10 and among fruit from 2.5R 2/5 to 5R 4/10. The fruit color in the FIG. 3 is shown as 5R 4/10. No other variety was producing fruit at that time. Compared to measurements of fruit color of other varieties taken in other years, the color of 'Schwartze' fruit would be slightly darker than 'Benton' and 'Sumas' and slightly larger than 'Puget Reliance' and 'Totem'. The length of the fruit average 39 mm long, 35.7 mm wide and 31.5 mm thick. The fruit does not display a "neck". There are some achenes present under the calyx segments, but none within 5 mm of the point where the calyx attaches to the fruit. The surface of the fruit under the calyx is red. The fruit is usually solid or has a small hollow. A comparison of fruit characteristics appears in Table 4 below.

TABLE 4

Comparison of Fruit Characteristics

| | Soluble Solids (%) | pH | Titractable acidity (citric acid) | Anthocyanins (μg/g) |
|---|---|---|---|---|
| Schwartz | 8.47 a | 3.13 a | 0.698 a | 476 b |
| Hood | 8.70 a | 3.21 a | 0.490 a | 583 a |
| Puget Reliance | 7.30 b | 3.03 a | 0.602 a | 390 c |
| Redcrest | 6.60 b | 3.00 a | 0.574 a | 624 a |
| Totem | 8.07 a | 3.11 a | 0.774 a | 525 b |

Means of three 10 g samples.
Mean separation in columns by Duncan's multiple range test, P < 0.05.
Schwartze had greater soluble solids than 'Redcrest' and 'Puget Reliance'. There were no differences among these cultivars for pH and titratable acidity. 'Schwartz' had similar concentration of anthocyanins as 'Totem'.

Flower: The flower and the fruit of 'Scheartze' are borne completely beneath the leaf canopy. This is in contrast to 'Independence' which has the flowers showing above the leaf canopy. The flowers are perfect with a cymose inflorescence, perigynous, calyx saucer-like, hypanthium narrow. See *Flora of the Pacific Northwest*, University of Washington Press, p. 211. There has been no noted fundamental difference among strawberry (Fragaria) clones in the shape of flowers. The flowers have five white petals with a minimum size of 10 mm and a maximum size of 35 mm. The petals are longer than the calyx segments. The calyx is flat when the flowers are open. There is an average of 9 fruit/scape. There are five sepals per fruit, which are subdivided into segments. The number of segments per fruit averaged 12.75. The calyx is pubescent and reflexed. The diameter of the calyx of ripe fruit averaged 35.75 mm with a diameter of the attachment to the fruit of 8.3 mm. The color of the calyx was 5GY 4/4. The external color of the fruit at its highest point averaged 5R 3/7, but varied within a fruit from 2.5R 3/7 to 5R 4/10. The internal color was measured at the apex of a longitudinal slice of the fruit. The internal color was 7.5R 5/10. The core of the fruit was white and the connections to the achenes are white, however, this becomes more red as the fruit ripens more fully. The L*, a* and b* color values for the petals were measured with a Minolta color meter 200b tristimulus colorimeter calibrated to a standard white plate supplied by the manufacturer. The color of the petals was measured as L*=91.3, a*=3.2, and b*= 6.5 which most closely resembles the white group 155D of The Royal Horticultural Society Colour Chart. This chart was used in place of the Munsell color chart for the color value of the petal because it includes a better representation of "white" colors. The flowers had no detectable fragrance. The number of flowers per inflorescence averaged 9.2 flowers in 1999 and a 1998 planting at Puyallup in Washington.

The colors of the petiole and petiolules were 2.5GY 6/7. The color of most achenes was 8.2Y 6.6/11.0, but varied according to the exposure of the surface of the fruit. Achenes on the same fruit that were exposed, were colored 6.4R 2.0/5.2 (darker than the surrounding fruit flesh). Similarly, the external color of the fruit at its widest point averaged 5R 3/7 but varied within a fruit from 2.5R 3/7 to 5R 4/10. The internal color was measured at the apex of a longitudinal slice of the fruit. The internal color was 7.5R 5/10. The core of the fruit is white and the connections to the achenes are white, however, this becomes more red as the fruit ripens more fully.

Bloom: The peak bloom at Puyallup was about May 22, 2000. This was three weeks later than 'Puget Reliance', U.S. Plant Pat. No. 9,310.

Disease and pest reaction: 'Schwartze' is susceptible to the strawberry aphid (*Chetosiphon fragaefolli*) an aphid vector of viruses. It is moderately susceptible to leaf scorch (Diplocarpon), but this has not appeared to decrease vigor. Common leaf spot [*Mycosphaerella fragariae* (Tul.) Lindau] and powdery mildew [*Spherotheca macularis* (Wallr. ex. Fr.)] have not been a problem at research plots at Puyallup, however, it has been noted on folige at Washington State University, Vancouver and in Fall, 1999 at some grower trials. 'Schwartze' has not been tested for resistance to specific races of red stele, causal organism (*Phytophthora fragaria* Hickman). Winter hardiness is unknown at this time.

I claim:

1. The new and distinct variety of strawberry plant described and illustrated and identified by the characteristics enumerated above.

* * * * *